(12) United States Patent
Jadhav et al.

(10) Patent No.: US 9,661,846 B2
(45) Date of Patent: May 30, 2017

(54) AGROCHEMICAL COMPOSITIONS

(71) Applicant: UPL Limited, Mumbai (IN)

(72) Inventors: Prakash Mahadeo Jadhav, Lawrenceville, NJ (US); Beth E. Sears, Lincoln University, PA (US); Vikram Rajnikant Shroff, Mumbai (IN)

(73) Assignee: UPL Limited, Mumbai (IN)

( * ) Notice: Subject to any disclaimer, the term of this patent is extended or adjusted under 35 U.S.C. 154(b) by 0 days.

(21) Appl. No.: 14/847,512

(22) Filed: Sep. 8, 2015

(65) Prior Publication Data

US 2016/0066570 A1 Mar. 10, 2016

Related U.S. Application Data

(60) Provisional application No. 62/047,162, filed on Sep. 8, 2014.

(51) Int. Cl.
*A01N 25/30* (2006.01)
*A01N 43/707* (2006.01)
*A01N 39/02* (2006.01)
*A01N 25/04* (2006.01)

(52) U.S. Cl.
CPC ............ *A01N 25/30* (2013.01); *A01N 25/04* (2013.01)

(58) Field of Classification Search
CPC ........ A01N 25/04; A01N 25/30; A01N 37/22; A01N 39/02; A01N 43/707
See application file for complete search history.

(56) References Cited

U.S. PATENT DOCUMENTS

| | | | | |
|---|---|---|---|---|
| 5,006,161 | A * | 4/1991 | Hasslin | A01N 37/18 504/149 |
| 6,235,300 | B1 * | 5/2001 | Brumbaugh | A01N 25/30 424/405 |
| 2011/0028323 | A1 * | 2/2011 | Shroff | A01N 41/06 504/127 |
| 2016/0002189 | A1 * | 1/2016 | Zierke | C07D 301/02 514/383 |

FOREIGN PATENT DOCUMENTS

WO  WO 2014108286  *  7/2014

* cited by examiner

*Primary Examiner* — Mina Haghighatian
(74) *Attorney, Agent, or Firm* — Yancy IP Law, PLLC

(57) ABSTRACT

The present invention relates to novel agrochemical compositions with enhanced bio-efficacy comprising at least one agrochemical active ingredient and an adjuvant composition.

5 Claims, No Drawings

AGROCHEMICAL COMPOSITIONS

CROSS-REFERENCE TO RELATED APPLICATIONS

This application claims the benefit, under 35 U.S.C. 119(e), of U.S. Provisional Application No. 62/047,162, filed Sep. 8, 2014, the contents of which are incorporated herein by reference

TECHNICAL FIELD OF THE INVENTION

The present invention relates to novel agrochemical combinations. More particularly, the present invention relates to novel agrochemical compositions with enhanced bio-efficacy comprising at least one agrochemical active ingredient and an adjuvant composition. The present invention further relates to a process for preparing such compositions and a method of using such compositions effectively.

BACKGROUND OF THE INVENTION

Soil-applied pre-plant incorporated and pre-emergence herbicides play an important role in the early control of weeds which in turn determine the overall development of the crop. Since the germination and early seedling growth are the most vulnerable stages in the weed's life cycle, effective administration of soil applicable pesticides becomes significant throughout the growing season of the crop. Hence it is critical to prevent the early weed establishment which is advantageous throughout the season.

The mode of action for most pre-emergence herbicides is the inhibition of certain phases of cell division during the seed germination process. As the weed seed germinates, the herbicide is absorbed by the root or shoots, cell division is blocked, growth is inhibited and eventually the immature seedling dies. Emerged weeds visible at the time of application are not controlled by pre-emergence herbicides, so to be effective; they must be applied prior to weed seed germination. Hence the timing of application of such herbicides is very crucial. Pre-emergent weed killers require water to activate them and carry the chemical down to the root systems of newly sprouted weeds. These herbicides don't stop weed germination, but rather interrupt the process before a sprout pushes through soil.

Pre-emergence herbicides or early post-emergence herbicides form the base of a chemical weed control method and are used primarily to control annual grasses and certain annual broadleaf weeds. They are most effective at controlling annual grassy weeds like crabgrass, foxtail, goose grass, and barnyard grass. Fair control of annual broadleaf weeds such as purslane, spurge, and oxalis can also be expected from most pre-emergents. The length of control depends on the specific chemical being used, physical and chemical properties, and soil factors such as texture, pH and moisture, and soil temperatures.

It has been noted that there are many factors which play an important role in determining performance of an herbicide. The ability of herbicides to penetrate compacted soils varies. Also many herbicides may have a long half-life, but have poor extended residual weed control as their bioavailability to weed seeds and/or efficacy at low concentrations is low. Some are sensitive to sunlight and need to be mixed into the soil to minimize losses. Some are volatile and can be lost to evaporation, especially from wet soil. It has been observed that soil applied herbicides have a tendency to get deposited at the spraying location, which in turn limit the coverage area and availability of the active ingredient. Further, some herbicides tend to leach-out and also lead to formation of striation which again affects the efficacy of such pesticides. Water soluble herbicides get washed off site and cause environmental issues during heavy rain falls.

In addition, the successful development of any pesticide formulation depends upon the type of formulation and the auxiliary agents such as solvents, adjuvants, emulsifiers, wetting and dispersing agents which are typically required for the intended performance. Often the selection of these agents creates problems such as incompatibility of the pesticide with such components. These problems are very critical as they have a direct impact on physico-chemical stability as well as the bio-efficacy of the active ingredient.

Therefore there is a need in the art for improved soil-applied pesticide compositions which have better bioefficacy compared to the existing formulations.

Surprisingly inventors of the present invention found out that by using an adjuvant composition, the agrochemical formulations led to reduction in dosage of the active ingredient and/or better weed control.

OBJECTS OF THE INVENTION

It is an object of the present invention to provide novel agrochemical compositions with better weed control comprising at least one agrochemical active ingredient and an adjuvant composition.

Another object of the present invention is to provide novel agrochemical compositions comprising one or more agrochemical active ingredient and an adjuvant composition which results in reduction in dosage of the active ingredient thereby making it eco-friendly.

Yet another object of the present invention is to provide novel agrochemical compositions having improved coverage and deposition of the active ingredient on the soil surface, comprising one or more agrochemical active ingredient and an adjuvant composition.

Still further object of the present invention is to provide novel agrochemical compositions comprising one or more agrochemical active ingredient and an adjuvant composition.

SUMMARY OF THE INVENTION

The present invention relates to novel agrochemical combinations comprising at least one agrochemical active ingredient and an adjuvant composition.

The present invention provides novel agrochemical compositions comprising at least one agrochemical active ingredient and an adjuvant composition.

Further there is provided a process for the preparation compositions comprising at least one agrochemical active ingredient and an adjuvant composition.

In another aspect there is provided a method of weed control said method comprising applying to the plant locus a composition comprising at least one agrochemical active ingredient and an adjuvant composition.

The present invention further relates to the use of said composition comprising at least one agrochemical active ingredient and an adjuvant composition.

In particular, the present invention relates to novel agrochemical compositions comprising at least one agrochemical active ingredient and an adjuvant composition comprising at least one fatty acid, alkyl phenol alkoxylate and a polymer condensate of an alkyl phenol with methyl oxirane.

DETAILED DESCRIPTION OF THE INVENTION

Inventors of the present invention surprisingly found out that the spreading and wetting properties of a soil based agrochemical active ingredient can be enhanced by using an adjuvant composition which in turn resulted in enhanced efficacy of the composition. In particular the present invention provides novel herbicidal compositions with enhanced bioefficacy.

Bioefficacy is a measure of the biological efficacy of an active ingredient of an agrochemical formulation. In case of an herbicide, the activity is measured in terms of killing or control of the weed at a given dosage of the herbicide. For a given agrochemical herbicidal composition, the bioefficacy of an herbicide is determined by the minimum dosage required for complete kill or control of the weeds. The term enhanced efficacy indicates an enhancement in the intended activity of the active ingredient. The enhanced efficacy is expressed in terms of either a reduction in dosage of the active ingredient or better weed control.

In an embodiment of the present invention there is provided novel combination comprising at least one agrochemical active ingredient and an adjuvant composition.

In another embodiment of the present invention there is provided novel compositions comprising at least one agrochemical active ingredient and an adjuvant composition.

In another embodiment of the present invention, there is provided novel compositions comprising at least one agrochemical active ingredient and an adjuvant composition comprising at least one fatty acid, an alkyl phenol alkoxylate and a polymer condensate of an alkyl phenol with methyl oxirane.

In yet another embodiment of the present invention, the agrochemical active ingredient is selected from various classes of pesticides including fungicides, insecticides and herbicides.

In an embodiment of the present invention, the preferred agrochemical active ingredient is herbicide.

In another embodiment of the present invention there is provided novel compositions comprising at least one herbicide and an adjuvant composition comprising at least one fatty acid, an alkyl phenol alkoxylate and a polymer condensate of an alkyl phenol with methyl oxirane.

In an exemplary embodiment of the present invention the herbicide is selected from but not limited to a dinitroaniline herbicide such as oryzalin or pendimethalin, nitrophenyl ether herbicide such as oxyfluorfen, chloroacetanilide herbicide such as metolachlor and its isomers, triazinone herbicide such as metribuzine, amide herbicide such as napropamide and its isomer napropamide-M and combinations thereof.

In another embodiment of the present invention, the compositions may comprise from about from about 5% to about 90% by weight of the herbicide. In a preferred embodiment the composition may comprise from about 10% to about 80% by weight of the herbicide, more preferably from about 15% to about 75% by weight of the herbicide.

In an embodiment of the present invention the adjuvant composition comprises at least one fatty acid, an alkyl phenol alkoxylate and a polymer condensate of an alkyl phenol with methyl oxirane. The fatty acid comprises linear or branched, saturated or unsaturated fatty acids or mixtures thereof.

In an embodiment the composition may contain from about 0.1% to about 15% by weight of the adjuvant composition, preferably from about 1% to about 10%, more preferably from about 1% to about 5% by weight.

In another embodiment of the present invention the ratio of fatty acid and/or alkyl phenol alkoxylate to polymer condensate of an alkyl phenol with methyl oxirane of the adjuvant composition is not particularly limiting.

In an embodiment the agrochemical composition according to the present invention contains a dinitroaniline herbicide such as oryzalin. Oryzalin is a selective herbicide which affects physiological growth processes associated with seed germination. The herbicide can be applied for pre-emergence control of many annual grasses and broad-leaved weeds.

In a preferred embodiment the agrochemical composition according to the present invention contains from about 5% to about 90% by weight of oryzalin, more preferably from about 10% to about 75% by weight. The composition contains from about 0.1% to about 10% by weight of the adjuvant composition, more preferably from about 1% to about 5% by weight.

In an embodiment of the agrochemical composition according to the present invention contains a dinitroaniline herbicide such as pendimethalin. Pendimethalin is a selective herbicide absorbed by the roots and leaves. Affected plants die shortly after germination or following emergence from the soil and control many annual grasses and annual broad-leaved weeds. This herbicide can be applied pre-plant incorporated, pre-emergence, pre-transplanting, or early post-emergence.

In another embodiment, the agrochemical composition according to the present invention contains from about 5% to about 90% by weight of pendimethalin, more preferably from about 10% to about 75% by weight. The composition contains from about 0.1% to about 10% by weight of the adjuvant composition, more preferably from about 1% to about 5% by weight.

In an embodiment, the agrochemical composition according to the present invention contains an acetamide herbicide such as napropamide or its isomers. Napropamide is a selective systemic herbicide, absorbed by the roots, with translocation acropetally and inhibits root development and growth of the weeds. This herbicide can be applied for pre-emergence control of many annual grasses and broad-leaved weeds.

In another preferred embodiment the composition contains from about 5% to about 90% by weight of napropamide or napropamide-M, more preferably from about 10% to about 75% by weight. The composition contains from about 0.1% to about 10% by weight of the adjuvant composition, more preferably from about 1% to about 5% by weight.

In an embodiment of the present invention the composition contains a combination of more than one active ingredients and an adjuvant composition comprising at least one fatty acid, alkyl phenol alkoxylate and a polymer condensate of an alkyl phenol with methyl oxirane.

In another embodiment the composition contains a combination of two or more herbicides and an adjuvant composition comprising at least one fatty acid, alkyl phenol alkoxylate and a polymer condensate of an alkyl phenol with methyl oxirane.

In a preferred embodiment the composition contains a second herbicide.

In an embodiment, the second herbicide that can be present in the composition according to the present invention is selected from an isoxazolidinone herbicide, a urea herbicide, a triazine herbicide, a hydroxybenzonitrile herbicide, a thiocarbamate herbicide, a pyridazine herbicide, chloroacetanilide herbicides, benzoic acid herbicides, benzothiazole herbicides, carbanilate herbicides, cyclohexene oxime herbicides, picolinic acid herbicides, pyridine herbicides, quinolinecarboxylic acid herbicides, chlorotriazine herbicides, aryloxyphenoxypropionic herbicides, oxadiazolone herbicides, phenylurea herbicides, sulfonanilide herbicides, triazolopyrimidine herbicides, amide herbicides, pyridazine herbicides and dinitroaniline herbicides.

In yet another embodiment of the present invention, the second herbicide is selected from am amide herbicide allidochlor, amicarbazone, beflubutamid, benzadox, benzipram, bromobutide, cafenstrole, cyprazole, dimethenamid, dimethenamid-P, diphenamid, epronaz, etnipromid, fentrazamide, flucarbazone, flupoxam, fomesafen, halosafen, huangcaoling, isocarbamid, isoxaben, napropamide, napropamide-M naptalam, pethoxamid, propyzamide, quinonamid, saflufenacil, tebutam, tiafenacil, sulfonamide herbicide such as asulam, carbasulam, fenasulam, oryzalin, penoxsulam, pyroxsulam, anilides such as propanil, aryloxycarboxylic acids such as MCPA-thioethyl, aryloxyphenoxypropionates such as clodinafop-propargyl, cyhalofop-butyl, diclofops, fluazifops, haloxyfops and its esters, haloxyfop-P and its esters, quizalofops, chloroacetamides such as acetolochlor, alachlor, butachlor, dimethenamid, metolachlor, propachlor, cyclohexanedione oximes such as alloxydim, butroxydim, clethodim, cloproxydim, cycloxydim, profoxydim, sethoxydim, tepraloxydim, tralkoxydim, benzamides such as isoxaben, benzoic acid derivatives such as dicamba, ethofumesate, dinitroanilines such as benfluralin, butralin, chlornidine, dinitramine, dipropalin, ethalfluralin, fluchloralin, isopropalin methalpropalin, nitralin, oryzalin, pendimethalin, prodiamine, profluralin, trifluralin, diphenyl ethers such acifluorfen, aclonifen, bifenox, chlomethoxyfen, chlornitrofen, etnipromid, fluorodifen, fluoroglycofen, fluoronitrofen, fomesafen, fucaomi, furyloxyfen, halosafen, lactofen, nitrofen, nitrofluorfen, oxyfluorfen, organophosphorus herbicides such as glufosinate and glyphosate, hydroxybenzonitriles such as bromoxynil, imidazolinones such as fenamidone, imazapic, imazamox, imazapic, imazapyr, imazethapyr, imazaquin, isoxazolidinones such as clomazone paraquat as bypyridylium, phenyl carbamates such as desmedipham, phenmedipham, phenylpyrazoles such as pyraflufen-ethyl, phenylpyrazolines such as pinoxaden, pyridinecarboxylic acids or synthetic auxins such as picloram, clopyralid, and triclopyr, pyrimidinyloxybenzoics such as bispyrtbac-sodium, sulfonyureas such as amidosulfuron, azimsulfuron, bensulfuron-methyl, chlorsulfuron, flazasulfuron, foramsulfuron, flupyrsulfuron-methyl-sodium, nicosulfuron, rimsulfuron, sulfosulfuron, tribenuron-methyl, trifloxysurlfuron-sodium, triflusulfuron, tritosulfuron, triazolopyrimidines such as penoxsulam, metosulam, florasulam, triketones such as mesotriones, sulcotrione, ureas such as diuron, linuron, phenoxycarboxylic acids such as 2,4-D, MCPA, MCPB, mecoprops and triazines such as atrazine, simazine and terbuthylazine.

The composition according to the present invention can further comprise other agronomically suitable excipients such as other surfactants, solvents, pH modifiers, viscosity modifiers (rheology modifiers), crystallisation inhibitor, antifoam agents, dispersing agents, wetting agents, humectants, emulsifiers, anticaking agent, suspending agents, spray droplet modifiers, pigments, antioxidants, UV protectants, compatibilizing agents, sequestering agents, neutralizing agents, corrosion inhibitors, dyes, odorants, spreading agents, penetration aids, lubricants, sticking agents, thickening agents, freezing point depressants, antimicrobial agents, and the like. The composition content of these auxiliary excipients is not particularly limiting and may be determined by a skilled technician in the art according to the conventional protocols.

In an embodiment of the present invention, the surfactants that can be additionally added to the compositions are selected from nonionic and/or anionic surfactants.

Examples of nonionic surfactants comprise alkylphenol alkoxylates, alcohol alkoxylates, fatty amine alkoxylates, polyoxyethylene glycerol fatty acid esters, castor oil alkoxylates, fatty acid alkoxylates, fatty amide alkoxylates, fatty polydiethanolamides, lanolin ethoxylates, fatty acid polyglycol esters, isotridecyl alcohol, fatty amides, methylcellulose, fatty acid esters, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers (polyethylene oxide/polypropylene oxide block copolymers) and mixtures thereof. Preferred nonionic surfactants are fatty alcohol ethoxylates, alkyl polyglycosides, glycerol fatty acid esters, castor oil alkoxylates, fatty acid alkoxylates, fatty amide alkoxylates, lanolin ethoxylates, fatty acid polyglycol esters and ethylene oxide/propylene oxide block copolymers and mixtures thereof such as for example Pluronic P-104.

Examples of anionic surfactants include alkylaryl sulfonates, phenyl sulfonates, alkyl sulfates, alkyl sulfonates, aryl alkyl sulfonates, alkyl ether sulfates, alkylaryl ether sulfates, alkyl polyglycol ether phosphates, polyaryl phenyl ether phosphates, alkyl sulfosuccinates, olefin sulfonates, paraffin sulfonates, petroleum sulfonates, taurides, sarcosides, salts of fatty acids, alkylnaphthalenesulfonic acids, naphthalenesulfonic acids and lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, alkyl phosphates, alkylaryl phosphates, for example tristyryl phosphates, and also polycarboxylates, such as, for example, polyacrylates, maleic anhydride/olefin copolymers, including the alkali metal, alkaline earth metal, ammonium and amine salts of the substances mentioned above and mixtures thereof. Preferred anionic surfactants are those which carry at least one sulfonate group, and in particular their alkali metal and their ammonium salts and mixtures thereof.

In another embodiment the surfactants can be selected from a blend of alkylbenzene sulfonate and polyoxyalkylene copolymers such as AU-545-80.

In an embodiment of the present invention, the composition can comprise pH modifiers. Suitable pH modifiers comprise buffers. Examples of buffers are alkali metal salts of weak inorganic or organic acids, such as, for example, phosphoric acid, boric acid, acetic acid, propionic acid, citric acid, fumaric acid, tartaric acid, oxalic acid and succinic acid.

In an embodiment of the present invention, solvents suitable for use in the compositions of the present invention include water, aromatic solvents (for example Solvesso products, xylene), alcohols (for example methanol, butanol, pentanol, benzyl alcohol), ketones (for example cyclohexanone, gamma-butyrolactone), pyrrolidones (NMP, NOP), ketonic solvents, glycols, acetates (glycol diacetate), carbonates such as propylene carbonates, fatty acid dimethylamides (for example N, N dimethyl octanamide, N, N dimethyl decanamide, Hallcomid), fatty acids fatty acid esters and amino carboxylic acid esters (polarclean). In principle, solvent mixtures can also be used.

In an embodiment the compositions of the present invention comprises a crystallisation inhibitor which is usually employed for this purpose in agrochemical compositions.

In another embodiment of the present invention, the compositions comprise antifoaming agents selected from non-silicone or silicone based antifoaming agents for example AF-100.

In an embodiment of the present invention, the compositions comprise rheology modifier (or a viscosity modifying additive). Suitable compounds are all those compounds usually employed for this purpose in agrochemical compositions. Examples include bentonites, attapulgites, polysaccharides, such as xanthan gum and kelzan gum.

In another embodiment of the present invention, the compositions comprise antifreeze agents. Suitable antifreeze agents are liquid polyols, for example ethylene glycol, propylene glycol or glycerol.

In yet another embodiment of the present invention, the compositions comprise dispersing agents. Preferred dispersants are of anionic or nonionic nature and selected, for example, from polyethylene glycol/polypropylene glycol block copolymers, polyethylene glycol alkyl ethers, polypropylene glycol alkyl ethers, polyethylene glycol/polypropylene glycol ether block copolymers, alkylaryl phosphates, for example tristyryl phosphates, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, polycarboxylates, such as, for example, polyacrylates, maleic anhydride/olefin copolymers including the alkali metal, alkaline earth metal, ammonium and amine salts of the substances mentioned above.

In another embodiment of the present invention, the compositions comprise wetting agents. Preferred wetting agents are of anionic or nonionic nature and selected, for example, from naphthalenesulfonic acids including their alkali metal, alkaline earth metal, ammonium and amine salts, fatty alcohol ethoxylates, alkyl polyglycosides, glycerol fatty acid esters, castor oil alkoxylates, fatty acid alkoxylates, fatty amide alkoxylates, fatty polydiethanolamides, lanolin ethoxylates and fatty acid polyglycol esters.

In an embodiment of the present invention the compositions comprise a humectant selected from polyols like sucrose, glycerin or glycerol, triethylene glycol, tripropylene glycol, and propylene glycol.

In an embodiment there is provided a process for the preparation of compositions comprising at least one agrochemical active ingredient and an adjuvant composition comprising at least one fatty acid, alkyl phenol alkoxylate and a polymer condensate of an alkyl phenol with methyl oxirane said process comprising the steps of:
a) Preparing a slurry of active ingredient;
b) adding the adjuvant composition;
c) adding other customary excipients if required; and
d) milling the slurry to desired particle size using suitable equipment.

In an embodiment of the present invention the step of preparing the slurry and the step of milling the slurry are not particularly limiting.

In another embodiment of the present invention the process of adding the ingredients can be in any order.

The compositions according to the present invention may be preferably formulated as liquid compositions such as soluble liquids, emulsifiable liquids, suspension concentrates, micro-emulsions, emulsions oil-in-water or water-in-oil, suspo-emulsions, etc. The processes for preparing such compositions are known in the art and are not particularly limiting.

The composition according to the present invention can also be prepared by tank-mixing the active ingredient with the adjuvant composition or alternatively may be sold as a kit of parts containing actives and other ingredients that may be mixed prior to spraying or a ready mix kit of parts containing premixed ingredients and actives described above.

In another embodiment of the present invention there is provided a method to control unwanted plants or to influence the growth of plants by treating said plants in the field with an effective amount of a herbicidal composition comprising at least one agrochemical active ingredient and an adjuvant composition.

In yet another embodiment of the present invention there is provided a method to control unwanted plants or to influence the growth of plants by treating said plants in the field with an effective amount of a herbicidal composition comprising a combination of two or more agrochemical active ingredients and an adjuvant composition.

The invention shall now be described with reference to the following specific examples. In the examples the adjuvant composition of the present invention is referred to as AU-376. It should be noted that the examples appended below illustrate rather than limit the invention and that those skilled in the art will be able to design many alternative embodiments without departing from the scope of the present invention.

EXAMPLES

General Composition

| Ingredient | % (w/w) |
|---|---|
| Active ingredient | 10-80 |
| Humectant | 3-5 |
| adjuvant composition (AU-376) | 2-5 |
| antifreeze agent | 5-10 |
| other ingredients* | 5-10 |
| Solvent | 0-20 |
| water | q.s. |

*other ingredients may include wetting agent, dispersing agent, pH modifier, anti-caking agent, rheology modifier, stabilizer, antifoam, biocide, emulsifier etc.

Example 1

A composition of oryzalin according to the present invention was prepared as follows:

| Ingredient | % (w/w) |
|---|---|
| Oryzalin | 34.1 |
| glycerin | 3.6 |
| AU-376 | 2.0 |
| AF-100 | 0.4 |
| Atplus 401 | 6.6 |
| Propylene glycol | 5.3 |
| Kelzan gum | 0.2 |
| Zeosyl | 0.6 |
| water | 47.4 |

The composition may be prepared by a process used for making a conventional Suspension Concentrate (SC).

In an example, following process was followed:

Step 1: Preparation of technical slurry
- a) Mix required quantity of water, antifreeze agent in a vessel.
- b) Add required quantity of AU-376 and the listed ingredients under stirring and continue to stir to homogenize.
- c) Add oryzalin under continued stirring to form slurry Step 2: wet milling
- a) Mill the homogenized slurry to desired particle Step 3: Gumming
To the above milled product, add required quantity of Kelzan gum to attain required viscosity of the suspension Step 4: filtration
Filter using suitable filter.

Example 2

A composition of oryzalin according to the present invention was prepared as follows:

| Ingredient | % (w/w) |
| --- | --- |
| Oryzalin | 34.1 |
| glycerin | 3.3 |
| AU-376 | 2.5 |
| AF-100 | 0.4 |
| Atplus 401 | 4.9 |
| Pluronic P-104 | 1.7 |
| Propylene glycol | 4.9 |
| Kelzan gum | 0.2 |
| Zeosyl | 0.6 |
| water | 47.4 |

Example 3

A composition of oryzalin according to the present invention was prepared as follows:

| Ingredient | % (w/w) |
| --- | --- |
| Oryzalin | 63.0 |
| glycerin | 8.0 |
| AU-376 | 3.9 |
| AF-100 | 0.7 |
| Atplus 401 | 3.5 |
| Pluronic P-104 | 2.1 |
| Propylene glycol | 6.2 |
| Kelzan gum | 0.2 |
| water | 12.4 |

Example 4

A composition of oryzalin according to the present invention was prepared as follows:

| Ingredient | % (w/w) |
| --- | --- |
| Oryzalin | 15.0 |
| glycerin | 3.3 |
| AU-376 | 2.5 |
| AF-100 | 0.4 |
| Pluronic(P-104) | 6.6 |
| Propylene glycol | 4.9 |
| Kelzan gum | 0.2 |
| water | 67.1 |

Example 5

Composition of Surflan AS which is treated as comparative sample for study of efficacy of composition according to the scope of the invention:

| Ingredient | % (w/w) |
| --- | --- |
| Oryzalin | 43.12 |
| Polyethylene glycol | 7.0 |
| Biocide | 0.10 |
| AF-100 | 0.10 |
| kelzan gum | 0.30 |
| Atplus 401 | 6.0 |
| glycerin | 3.00 |
| Grinding aid | 1.00 |
| water | q.s |

Example 6

A composition comprising Pendimethalin according to the present invention was prepared as follows:

| Ingredient | % (w/w) |
| --- | --- |
| Pendimethalin technical (96.5) | 41.2 |
| AU-545-80 | 11.0 |
| AU-376 | 2.0 |
| Hallcomid | 5.8 |
| Solvesso | 35 |
| Water | q.s. |

Example 7

A composition comprising Pendimethalin according to the present invention was prepared as follows:

| Ingredient | % (w/w) |
| --- | --- |
| Pendimethalin technical (96.5) | 41.0 |
| AU-545-80 | 12.0 |
| AU-376 | 2.0 |
| Aromatic 200 ND | 40.0 |
| Propylene carbonate | 5.0 |

Example 8

A composition comprising Pendimethalin according to the present invention was prepared as follows:

| Ingredient | % (w/w) |
| --- | --- |
| Pendimethalin technical (96.5) | 41.0 |
| AU-545-80 | 14.0 |
| AU-376 | 2.0 |
| Aromatic 200 ND | 38.0 |
| glycol diacetate | 5.0 |

Example 9

A composition comprising Pendimethalin according to the present invention was prepared as follows:

| Ingredient | % (w/w) |
|---|---|
| Pendimethalin technical (96.5) | 16 |
| AU-545-80 | 7.0 |
| AU-376 | 1.5 |
| Solvesso | 35.0 |
| glycol diacetate | 7.0 |
| Water | q.s. |

Example 10

Composition of Pendimethalin EC as per U.S. Pat. No. 4,450,001 which is treated as comparative sample for study of efficacy of composition according to the scope of the invention:

| Ingredient | % (w/w) |
|---|---|
| Pendimethalin technical (96.5) | 41.2 (39.8% AI) |
| Maleic acid half ester of 1,4-butanediol inititated polybutylene glycol ethoxylate | 10.0 |
| Calcium dodecyl benzene sulfonate | 2.0 |
| Solvesso | 35 |
| Water | q.s. |

Example 11

A composition comprising Napropamide according to the present invention was prepared as follows:

| Ingredient | % (w/w) |
|---|---|
| Napropamide | 40.0 |
| AU-545-80 | 11.0 |
| AU-376 | 2.0 |
| Hallcomid | 5.8 |
| Solvesso | 35 |
| Water | q.s. |

Table 1 below discloses some more compositions which can be prepared according to the present invention.

TABLE 1

| | Oxyfluorfen | Metribuzine | Napropamide-M |
|---|---|---|---|
| Active ingredient 1 | (34.08 g) | (32.8 g) | (19.8 g) |
| Humectant | 3-5 | 3-5 | 3-5 |
| AU-376 | 2-5 | 2-5 | 2-5 |
| Antifreeze | 4-10 | 4-10 | 4-10 |
| Other ingredients | 5-10 | 5-10 | 5-10 |
| Organic solvent | 5-20 | 5-20 | 5-20 |
| water | q.s. | q.s. | q.s. |

Bio-Efficacy Test:

Field trials were conducted for the compositions of present invention to evaluate herbicidal activity. The samples were sprayed on different grasses and weeds incidence was checked for initial control at 14 days after treatment (14 DAT), and long term weed incidence as 60 days after treatment (60 DAT).

Protocol:

Example 1 (3.2 lb/gal SC, 32% w/w formulation) of the present invention was tested for weed control against Example 5 (Oryzalin 4 lb/gal SC, 40% w/w formulation). Both the samples were diluted to spray dilution and % weed incidence was measured.

The results of the field trial are tabulated below (Table 2).

TABLE 2

| | % weed incidence | | | | |
|---|---|---|---|---|---|
| Product | 0 Days | 14 Days | 29 Days | 60 Days | Assessment |
| Signalgrass | | | | | |
| Example 1 | 100 | 0.5 | 10 | 4 | Initial as well as long term weed control is better |
| Example 5 | 100 | 5.3 | 16.3 | 6.3 | |
| Amaranth | | | | | |
| Example 1 | 100 | 0.3 | 5.3 | 1 | Excellent long term (residual) weed control |
| Example 5 | 100 | 0.8 | 10 | 6.3 | |
| Goosegrass | | | | | |
| Example 1 | 100 | 0.5 | 8.8 | 3 | Fair weed control |
| Example 5 | 100 | 3 | 11.3 | 5 | |

In the field trial, herbicidal activity of Oryzalin composition according to the present invention is tested against Example 5 (a sample prepared according to the prior art) in signal grass, amaranth and goosegrass. The data shows that in Example 1, all the three weeds exhibit lesser weed incidence at the 14 days evaluation timeframe. The incidence in case of the composition of Example 1 is 0.5% against 5.3% with composition of Example 5 in case of Signal grass, and 0.5% against 3% in case of Goosegrass. When the incidence was measured after 60 days to check the long term effect (residual weed control), composition of Example 1 was found to exhibit weed incidence of 4% against 6.3% for composition of Example 5 in case of Signalgrass and 1% against 6.3% in case of Amaranth. The compositions of the present invention led to a reduction in dosage of the active ingredient. A better residual weed control was observed at around 20% lesser dosage of the active ingredient (3.2 lb/gal as against 4 lb/gal). The compositions of the present invention are thus eco-friendly as the better weed control is obtained with less amount of the active ingredient per acre.

Field Trial 2:

Protocol:

Dormant weed control in almond field was tested using the compositions according to the present invention. The efficacy of the compositions was tested against Swinecress, Shepherd's purse, California burr clover and Common malva. Composition of Example 6 of the present invention was tested for weed control against Satellite (market sample of pendimethalin 38.7%, EC) and composition of Example 10 prepared as per prior art. The plots were evaluated for the weed control on 65 and 96 days after treatment. The results are tabulated in the Table 3.

TABLE 3

| Product | % weed control | | | | | |
|---|---|---|---|---|---|---|
| | 65 Days (1.9 lb ai) | 96 Days (1.9 lb ai) | 65 Days (3.8 lb ai) | 96 Days (3.8 lb ai) | 65 Days (5.7 lb ai) | 96 Days (5.7 lb ai) |
| Swinecress | | | | | | |
| Example 6 | 97.5 | 31.3 | 100 | 58.8 | 100 | 77.5 |
| Satellite | 97.5 | 7.5 | 98.8 | 20 | 100 | 55 |
| Example 10 | 90 | 5.5 | 95 | 18 | 97 | 47 |
| Shepherd's purse | | | | | | |
| Example 6 | 65 | 28.8 | 92.5 | 53.8 | 96.3 | 73.8 |
| Satellite | 15 | 8.8 | 72.5 | 22.5 | 85 | 48.8 |
| Example 10 | 10 | 5.7 | 65 | 17 | 98 | 35 |
| California burr clover | | | | | | |
| Example 6 | 99 | 95 | 95 | 87.5 | 100 | 100 |
| Satellite | 75.5 | 31.5 | 91 | 75 | 94 | 50 |
| Example 10 | 67.8 | 18.8 | 80 | 69 | 90 | 62 |
| Common malva | | | | | | |
| Example 6 | 100 | 25 | 100 | 100 | 100 | 100 |
| Satellite | 94 | 12.8 | 98.8 | 10 | 100 | 72.5 |
| Example 10 | 85 | 5.5 | 90 | 23 | 85 | 65 |

In the field trial, it has been observed that the composition according to the present invention exhibits better bio-efficacy. While other treatments provided erratic control on some weed species, composition of Example 6 provided better control on most of the weeds tested. It has been observed that even at a dosage of 1.9 lb/acre the composition according to the present invention provided acceptable weed control compared to known formulations. It can therefore be concluded that the formulation of the present invention comprising the pesticide with the adjuvant compositions provides better weed control compared to the conventional formulation even at a lower concentration of the pesticide. Thus greater weed control efficacy is demonstrated on susceptible species.

The invention claimed is:

1. An agrochemical composition comprising:
   (i) at least one herbicide selected from the group consisting of oryzalin, pendimethalin, oxyfluorfen, metolachlor and its isomers, metribuzine, and napropamide and its isomers in an amount of about 5% to about 90% by weight of the composition and
   (ii) an adjuvant composition in an amount from about 0.1% to about 15% by weight of the agrochemical composition, said adjuvant composition comprising (i) at least one fatty acid, (ii) at least one alkyl phenol alkoxylate and (iii) at least a polymer condensate of an alkyl phenol with methyl oxirane.

2. The agrochemical composition of claim 1, wherein said agrochemical composition is a liquid composition.

3. The agrochemical composition of claim 1, wherein said agrochemical composition comprises a second herbicide.

4. A process for preparation of an agrochemical composition according to claim 1, wherein said process comprising the steps of:
   a. Preparing a slurry of active ingredient;
   b. adding an adjuvant composition comprising at least one fatty acid, at least one alkyl phenol alkoxylate and at least one polymer condensate of an alkyl phenol with methyl oxirane;
   c. adding other customary excipients if required; and
   d. milling the slurry to desired particle size using suitable equipment.

5. A method of weed control said method comprising applying to soil or plant locus an agrochemical composition as claimed in claim 1.

* * * * *